(12) United States Patent
Biard

(10) Patent No.: US 6,846,936 B2
(45) Date of Patent: Jan. 25, 2005

(54) 2-BUTYL-3-(4-[3(DIBUTYLAMINO) PROPOXY]BENZOYL)-5-NITRO-BENZOFURAN HYDROCHLORIDE AND PREPARATION THEREOF

(75) Inventor: Michel Biard, La Mure (FR)

(73) Assignee: Sanofi-Synthelabo, Paris (FR)

( * ) Notice: Subject to any disclaimer, the term of this patent is extended or adjusted under 35 U.S.C. 154(b) by 0 days.

(21) Appl. No.: 10/433,639

(22) PCT Filed: Dec. 10, 2001

(86) PCT No.: PCT/FR01/03900

§ 371 (c)(1),
(2), (4) Date: Jun. 4, 2003

(87) PCT Pub. No.: WO02/48078

PCT Pub. Date: Jun. 20, 2002

(65) Prior Publication Data

US 2004/0010032 A1 Jan. 15, 2004

(30) Foreign Application Priority Data

Dec. 11, 2000 (FR) ............................................ 00 16069

(51) Int. Cl.⁷ ....................... A61K 307/78; C07C 229/00
(52) U.S. Cl. ......................... 549/467; 560/23; 562/444
(58) Field of Search ........................ 549/467; 564/280, 564/305; 560/23

(56) References Cited

U.S. PATENT DOCUMENTS 5,223,510 A 6/1993 Gubin et al.

FOREIGN PATENT DOCUMENTS

EP 0 471 609 A 2/1992

OTHER PUBLICATIONS

Gutan, AL, 'Process for the preparation of dronedarone' CA 138:385296 (2003).*
Fino, N, 'A process for the preparation of 2–butyl–5–[mmethansulfonamido]benzofuran as an intermediate for the synthesis of dronedarone' CA 137:33205 (2002).*
Y. Oshishi et al; "Antibacterial activity and Polarographic Half–Wave Reduction Potential of 2–Nitrobenzo 'b!furans"; Chem. Pharm. Bull; vol. 33, No. 7, 1985, pp2854–2861; XP00156510.

* cited by examiner

Primary Examiner—Amelia A. Owens
(74) Attorney, Agent, or Firm—Paul E. Dupont; Michael D. Alexander

(57) ABSTRACT

The invention relates to 2-butyl-3-(4-[3-(dibutylamino) propoxy]benzoyl-5-nitrobenzofuran hydrochloride, to its preparation and to its use as synthetic intermediate, in particular in preparing 2-butyl-3-(4-[3-(dibutylamino) propoxy]benzoyl)-5-nitrobenzofuran, itself an intermediate for dronedarone.

28 Claims, No Drawings

2-BUTYL-3-(4-[3(DIBUTYLAMINO) PROPOXY]BENZOYL)-5-NITRO-BENZOFURAN HYDROCHLORIDE AND PREPARATION THEREOF

The present invention relates, generally, to an aminoalkoxybenzoyl derivative in the salt form, to its process of preparation and to its use as synthetic intermediate.

More specifically, a subject matter of the invention is the 2-butyl-3-(4-[3-(dibutylamino)-propoxy]benzoyl)-5-nitrobenzofuran hydrochloride of formula:

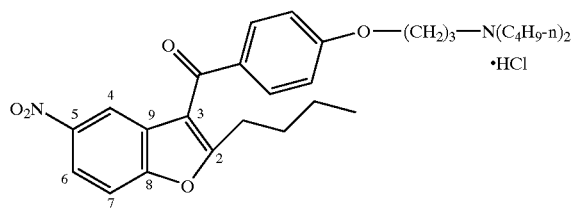

hereinafter referred to as "Compound A hydrochloride".

This compound has proved to be particularly useful as intermediate for the preparation of 2-butyl-3-(4-[3-(dibutylamino)propoxy]benzoyl)-5-nitrobenzofuran, hereinafter referred to as "Compound A".

The latter can itself be widely used as intermediate in the preparation of various products, in particular for the final synthesis of (aminoalkoxybenzoyl)benzofuran derivatives, in particular of 2-butyl-3-(4-[3-(dibutylamino)propoxy] benzoyl)-5-(methanesulfonamido)benzofuran, commonly called dronedarone, and its pharmaceutically acceptable salts.

This (methanesulfonamido)benzofuran derivative and its pharmaceutically acceptable salts have been disclosed in patent EP 0471609, as well as its therapeutic applications. This compound has been shown to be particularly advantageous in the cardiovascular field, in particular as antiarrhythmic agent.

The abovementioned patent EP 0471609 has also reported a process for the preparation of 3-[4-(aminoalkoxy)benzoyl] benzofuran or -benzo[b]thiophene derivatives by attachment of an aminoalkoxybenzoyl chain to a benzofuran or benzo [b]thiophene derivative, according to which process a benzoyl group comprising, in the para position, an oxygen protected by a methyl group is first added to the benzofuran or benzo[b]thiophene derivative in question, deprotection is carried out to regenerate the hydroxyl functional group and, finally, the desired aminoalkyl chain is introduced.

More specifically, this process, applied to the preparation of Compound A, comprises the sequence of stages below:

a) reaction of 2-butyl-5-nitrobenzofuran with anisoyl chloride in the presence of tin tetrachloride according to the conditions of the Friedel-Crafts reaction and hydrolysis to form 2-butyl-3-(4-methoxybenzoyl)-5-nitrobenzofuran, b) demethylation of the compound thus obtained in the presence of 2.25 molar equivalents of aluminum chloride and hydrolysis to form 2-butyl-3-(4-hydroxybenzoyl)-5-nitrobenzofuran, c) condensation of the compound thus obtained with 1-chloro-3-(dibutylamino)propane in the presence of potassium carbonate to give the desired Compound A.

However, this process is not without exhibiting certain disadvantages due in particular to the use of aluminum chloride. This is because the use of this process on the industrial scale results in large discharges of aluminum hydroxide, the treatment of which, for the purpose of preventing problems of pollution, proves to be expensive. In addition, the use of 2-butyl-3-(4-methoxybenzoyl)-5-nitrobenzofuran should be avoided because of its mutagenic properties.

Finally, the desired compound is produced, according to this three-stage process, with a maximum yield of only 60% from 2-butyl-5-nitrobenzofuran.

The search for an industrial process for the preparation of Compound A employing a minimum number of synthetic stages from 2-butyl-5-nitrobenzofuran while avoiding the use of aluminum chloride consequently remains of unquestionable interest.

J. Med. Chem., 1984, 27, 1057–1066, has reported a more convergent method for attaching an aminoalkoxybenzoyl chain to a benzo[b]thiophene derivative without passing through a stage of protection of the hydroxyl functional group. However, this process still provides, on page 1064, for the use of aluminum chloride in particularly high amounts since they are of the order of 9 molar equivalents.

According to this method, the benzo[b]thiophene derivative in question is condensed, in an organic phase composed of dichloroethane, with the hydrochloride of the chloride of the aminoalkoxybenzoyl derivative, this taking place in the presence of aluminum chloride. After hydrolysis, the hydrochloride of the desired 3-[4-(aminoalkoxy)benzoyl]benzo[b] thiophene derivative is recovered, partly from the organic phase and partly from the aqueous phase by three extractions with chloroform, and then treated with sodium hydroxide.

In the context of the development of the present invention, this process was applied to the preparation of Compound A by employing the following stages:

treatment of 2-butyl-5-nitrobenzofuran by means of 4-[3-(dibutylamino)propoxy]benzoyl chloride hydrochloride in the presence of 9 molar equivalents of aluminum chloride, this taking place in an organic phase, hydrolysis, recovery of Compound A hydrochloride and treatment with sodium hydroxide to form the desired Compound A.

However, this process proved to be unsuitable at the industrial level because, first, of the huge amount of aluminum hydroxide thus produced and, secondly, of the high level of impurities collected and, consequently, of the low yield of the desired Compound A provided (20 to 30%).

In point of fact, surprisingly, it has been found that it is possible, starting from 2-butyl-5-nitrobenzofuran and using appropriate amounts of a Lewis acid in a Friedel-Crafts reaction, to obtain Compound A hydrochloride with a high yield, since it is greater than 90%, it being possible for this hydrochloride to be recovered in a notably advantageous way since it is virtually all found not in the aqueous phase, as might have been anticipated, but in the organic phase used, which avoids the necessity to carry out several extractions of the same aqueous phase as in the prior process.

In addition, this hydrochloride can be employed with great ease in the preparation of Compound A, which can be produced, according to the invention, with yields of greater than 95%.

According to the invention, Compound A hydrochloride is prepared by reacting, in an organic phase, 2-butyl-5-nitrobenzofuran with 4-[3-(dibutylamino)propoxy]benzoyl chloride hydrochloride, this taking place in the presence of a Lewis acid as catalyst, and by hydrolyzing to form the desired compound, which is recovered in the organic phase.

The reaction, carried out according to the conditions of the Friedel-Crafts reaction, is usually carried out at ambient temperature and in an organic phase composed of one or more solvents chosen from halogenated or nonhalogenated hydrocarbons, preferably of aliphatic, alicyclic or aromatic type. Use is generally made of halogenated hydrocarbons, preferably chlorinated hydrocarbons, of aliphatic, alicyclic or aromatic type, such as, for example, dichloromethane, dichloroethane or chlorobenzene.

In addition, the Lewis acid can be aluminum chloride, zinc chloride, boron trifluoride, stannic chloride, titanium tetrachloride or, preferably, ferric chloride. A mixture of these may be used. This Lewis acid is used in amounts not exceeding 3 molar equivalents, in particular in a proportion of 2 to 3 molar equivalents, preferably 2.5 molar equivalents.

Finally, 4-[3-(dibutylamino)propoxy]benzoyl chloride hydrochloride is employed in a slight quantitative excess, such as, for example, in amounts of the order of 1 to 1.3 molar equivalents.

This chloride hydrochloride is a novel product, in the same way as other compounds involved in the preparation of Compound A hydrochloride.

However, patent EP 0471609 mentions, in its example 28, the individual case of the compound 1-chloro-4-(3-(di(n-butyl)amino)propoxy)benzoyl hydrochloride for its use in the synthesis of 2-(n-butyl)-3-[4-(3-(di(n-butyl)amino) propoxy)benzoyl]-7-carbethoxyindolizine hydrogen oxalate.

Consequently, another subject matter of the invention relates to the benzoyl derivatives of general formula:

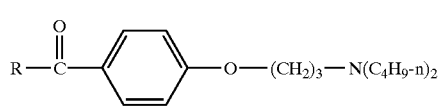

(2)

and to their hydrochloride, in which R represents chlorine or an —OR$_1$ group in which R$_1$ represents hydrogen or a C$_1$–C$_4$ alkyl group, with the exception of 1-chloro-4-(3-(di(n-butyl)amino)propoxy)benzoyl hydrochloride, as novel industrial products of use in particular as synthetic intermediates, for example for the preparation of Compound A hydrochloride.

Mention may be made, by way of example, of:

4-[3-(dibutylamino)propoxy]benzoic acid hydrochloride,
4-[3-(dibutylamino)propoxy]benzoyl chloride hydrochloride,
methyl 4-[3-(dibutylamino)propoxy]benzoate.

The invention also relates to the process for the preparation of the compounds of formula (2) above.

4-[3-(Dibutylamino)propoxy]benzoyl chloride hydrochloride and the other compounds of formula (2) can be prepared according to the sequence of stages below:

a) 1-dibutylamino-3-chloropropane is reacted with a C$_1$–C$_4$ alkyl p-hydroxybenzoate, for example methyl p-hydroxybenzoate, this taking place in the presence of a basic agent, such as an alkali metal carbonate, for example potassium carbonate, to produce a C$_1$–C$_4$ alkyl 4-[3-(dibutylamino)propoxy]benzoate of formula (2), for example methyl 4-[3-(dibutylamino)propoxy] benzoate, b) the ester thus obtained is saponified in the presence of an alkali metal hydroxide, for example sodium hydroxide, and then the salt thus formed is treated using hydrochloric acid to give 4-[3-(dibutylamino)propoxy] benzoic acid hydrochloride, c) the hydrochloride thus formed is then treated using a chlorinating agent, for example thionyl chloride, to produce the desired compound.

As mentioned above, Compound A hydrochloride can give access to Compound A.

Consequently, another subject matter of the invention relates to the preparation of Compound A by treatment of its hydrochloride using a basic agent, such as an alkali metal hydroxide, for example sodium hydroxide, an alkali metal carbonate or an alkali metal hydrogencarbonate, to produce the desired compound. Use is preferably made of an alkali metal hydrogencarbonate, such as sodium hydrogencarbonate.

According to a preferred use of the invention, Compound A is prepared without isolation of its hydrochloride formed as an intermediate, that is to say in the same medium in which this hydrochloride is prepared.

Consequently, according to an alternative for of the invention, Compound A is prepared by a process according to which, in an organic phase composed of one or more solvents chosen from halogenated or nonhalogenated hydrocarbons, 2-butyl-5-nitrobenzofuran is reacted with 4-[3-(dibutylamino)-propoxy]benzoyl chloride hydrochloride, this taking place in the presence of a maximum of 3 molar equivalents of a Lewis acid as catalyst, and the mixture is hydrolyzed to produce Compound A hydrochloride as an intermediate and without isolation, which product is recovered in the organic phase and is treated using a basic agent, providing the desired Compound A.

This method is particularly advantageous since it makes it possible to obtain Compound A directly from 2-butyl-5-nitrobenzofuran without any isolation of synthetic intermediate and with high yields, since they are of the order of 97% from the starting nitro derivative.

As indicated above, Compound A hydrochloride can be used in the preparation of dronedarone and its pharmaceutically acceptable salts.

Consequently, the invention also relates to Compound A hydrochloride as intermediate in the final synthesis of dronedarone and its pharmaceutically acceptable salts.

For example, this compound and its salts can be prepared starting from Compound A, itself obtained according to the invention from its hydrochloride, by employing a process comprising the sequence of stages below:

a) in an organic phase, composed of one or more solvents chosen from halogenated or nonhalogenated hydrocarbons, 2-butyl-5-nitrobenzofuran is reacted with 4-[3-(dibutylamino)propoxy]benzoyl chloride hydrochloride, this taking place in the presence of a maximum of 3 molar equivalents of a Lewis acid as catalyst, the mixture is hydrolyzed to produce Compound A hydrochloride as an intermediate and without isolation, which product is recovered in the organic phase and is treated using a basic agent to form Compound A, b) the Compound A obtained is hydrogenated in the presence of an appropriate catalyst, such as platinum oxide, which gives 5-amino-2-butyl-3-(4-[3-(dibutylamino)propoxy]-benzoylbenzofuran, c) the 5-aminobenzofuran derivative thus obtained is reacted with methanesulfonyl chloride or methanesulfonic anhydride, the reaction taking place in the presence of an acid acceptor, such as triethylamine, which gives dronedarone, which is reacted, if desired, with an organic or inorganic acid to form a pharmaceutically acceptable salt of this compound.

The above stages (c) and (d) are known stages which have been disclosed in the abovementioned patent EP 0471609.

The following nonlimiting examples illustrate the invention.

In these examples, the abbreviations used have the meanings reported below:
NMR: nuclear magnetic resonance
HPLC: high pressure liquid chromatography

PREPARATION

A. 1-Dibutylamino-3-chloropropane 288.4 g (3.392 mol) of 20% aqueous ammonia are introduced into a 1 l reactor and then 618 g (1.696 mol) of 1-dibutylamino-3-chloropropane hydrochloride (assay 66.5%) are added over 10 minutes and at ambient temperature (22±2° C.). The mixture is stirred for 45 minutes at ambient temperature and is left to separate by settling for 30 minutes. The lower aqueous phase (pH=11) is removed and the organic phase is washed with 300 ml of deionized water at ambient temperature. Stirring is carried out for 30 minutes, separation by settling is carried out for 30 minutes and the lower aqueous phase (pH=9) is removed.

In this way, 346.3 g of the desired compound are collected.

Yield: 99.4%.

EXAMPLE 1

Methyl 4-[3-(dibutylamino)propoxy]benzoate 200 g (1.3 mol) of methyl p-hydroxybenzoate and 1.6 l of N,N-dimethylformamide are introduced into a 2 l round-bottomed flask. The mixture is stirred and 232 g (1.66 mol) of potassium carbonate are added thereto. The mixture is heated to 100° C. and then the 1-dibutylamino-3-chloropropane prepared in stage A. above is introduced over 10 minutes. The reaction medium is maintained at 100±2° C. for 1 hour and is then cooled to 25° C. The inorganic salts are filtered off and rinsed with 2 times 50 ml of N,N-dimethylformamide and the filtrate is concentrated on a rotary evaporator up to a temperature of 85° C. and a pressure of 5 mmHg.

In this way, 472.7 g of the desired product are obtained in the form of a clear yellow oil.

Purity (HPLC) Desired compound: 99.7% Methyl p-hydroxybenzoate: 0.1% NMR spectrum (300 MHz) Solvent: CDCl$_3$ Concentration: 40 mg/ml Analysis temperature: 300K

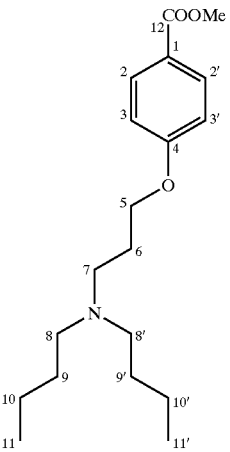

"Me" represents the methyl group.

| Chemical shifts δ ± 0.01 ppm | Multiplicity | Integration | Coupling constants \|J\| ± 0.5 Hz | Assignment |
|---|---|---|---|---|
| 7.97 | Doublet | 2 | $^3J_{H-H}$≈9.0 | H (2) and H (2') |
| 6.90 | Doublet | 2 | $^3J_{H-H}$≈9.0 | H (3) and H (3') |
| 4.06 | Triplet | 2 | $^3J_{H-H}$≈6.5 | OCH$_2$ (5) |
| 3.87 | Singlet | 3 | — | OCH$_3$ |
| 2.57 | Triplet | 2 | $^3J_{H-H}$≈7.0 | CH$_2$ (7) |
| 2.40 | Triplet | 4 | $^3J_{H-H}$≈7.0 | CH$_2$ (8) and CH$_2$ (8') |
| 1.90 | Quintet | 2 | $^3J_{H-H}$≈7.0 | CH$_2$ (6) |
| 1.39 | Multiplet (deformed quintet) | 4 | — | CH$_2$ (9) and CH$_2$ (9') |
| 1.28 | Multiplet (deformed sextet) | 4 | $^3J_{H-H}$≈7.0 | CH$_2$ (10) and CH$_2$ (10') |
| 0.87 | Triplet | 6 | $^3J_{H-H}$≈7.0 | CH$_3$ (11) and CH$_3$ (11') |

EXAMPLE 2

4-[3-(Dibutylamino)propoxy]benzoic acid hydrochloride 436.3 g of methyl 4-[3-(dibutylamino)propoxy]benzoate and 1.092 l of methanol are introduced into a 2 l round-bottomed flask. The mixture is stirred and 360 g (1.8 mol) of 20% sodium hydroxide are introduced over approximately 5 minutes.

The mixture is heated to 65° C. over approximately 30 minutes and is maintained at this temperature for 2 hours. The reaction medium is cooled to 30° C. and is concentrated on a rotary evaporator (bath temperature: 30° C., pressure 30 mmHg), which gives 937 g of residue which is diluted by addition of 2.8 l of deionized water. The solution is cooled to 10±2° C. and then, without exceeding 20° C., 260 ml (approximately 3 mol) of 36% hydrochloric acid are introduced.

It is confirmed that the pH is less than 1 and then the suspension is cooled to 10±2° C. This temperature is maintained for 30 minutes, the crystals formed are filtered off and the cake is washed with 2 times 200 ml of deionized water. The cake is subsequently dried in a ventilated oven at 50° C. to constant weight (24 hours).

In this way, 416.2 g of the desired compound are obtained in the form of a powder.

Yield: 100%. Purity (HPLC) Desired compound: 99.5% Methyl 4,-[3-(dibutylamino)propoxy]benzoate: 0.1% NMR spectrum (300 MHz) Solvent: CDCl$_3$ Concentration: 40 mg/ml Analysis temperature: 300K

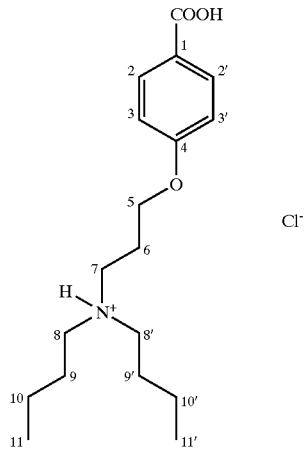

| Chemical shifts δ ± 0.01 ppm | Multiplicity | Integration | Coupling constants \|J\| ± 0.5 Hz | Assignment |
|---|---|---|---|---|
| 11.76 and 10.31 | 2 broad singlets | 2 | — | NH$^+$ and COOH |
| 7.93 | Doublet | 2 | $^3J_{H-H}$≈8.5 | H (2) and H (2') |
| 6.81 | Doublet | 2 | $^3J_{H-H}$≈8.5 | H (3) and H (3') |
| 4.10 | Triplet | 2 | $^3J_{H-H}$≈5.5 | OCH$_2$ (5) |
| 3.26 | Multiplet | 2 | — | CH$_2$ (7) |
| 3.04 | Multiplet | 4 | — | CH$_2$ (8) and CH$_2$ (8') |
| 2.38 | Multiplet | 2 | — | CH$_2$ (6) |
| 1.78 | Multiplet | 4 | — | CH$_2$ (9) and CH$_2$ (9') |
| 1.37 | Sextet | 4 | — | CH$_2$ (10) and CH$_2$ (10') |
| 0.93 | Triplet | 6 | — | CH$_3$ (11) and CH$_3$ (11') |

EXAMPLE 3
4-[3-(Dibutylamino)propoxy]benzoyl chloride hydrochloride 63.3 g (0.184 mol) of 4-[3-(dibutylamino)propoxy] benzoic acid hydrochloride, 300 ml of chlorobenzene and 2 drops of N,N-dimethylformamide are introduced into a round-bottomed flask. 43.8 g (0.368 mol) of thionyl chloride are introduced over approximately 45 minutes while maintaining the mixture under an inert atmosphere. The mixture is maintained at 85±1° C. for 1 hour and then approximately 115 g of a mixture of chlorobenzene and of thionyl chloride is distilled off under gradually increasing vacuum.

In this way, the desired compound is obtained in the form of a powder and of lumps which are pale yellow in color.

NMR spectrum Solvent: CDCl$_3$ Concentration: 40 mg/ml Analysis temperature: 300K

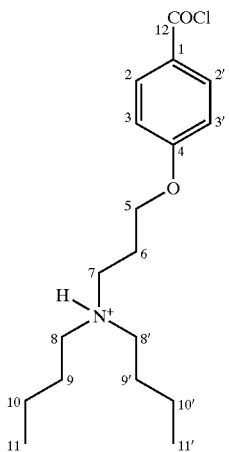

| Chemical shifts δ ± 0.01 ppm | Multiplicity | Int gration | Coupling constants \|J\| ± 0.5 Hz | Assignment |
|---|---|---|---|---|
| 12.19 | Broad singlet | 1 | — | NH$^+$ |
| 8.03 | Doublet | 2 | $^3J_{H-H}$≈9.0 | H (2) and H (2') |
| 6.91 | Doublet | 2 | $^3J_{H-H}$≈9.0 | H (3) and H (3') |
| 4.18 | Triplet | 2 | $^3J_{H-H}$≈5.5 | OCH$_2$ (5) |
| 3.21 | Multiplet | 2 | — | CH$_2$ (7) |
| 3.02 | Multiplet | 4 | — | CH$_2$ (8) and CH$_2$ (8') |
| 2.42 | Multiplet | 2 | — | CH$_2$ (6) |
| 1.79 | Multiplet | 4 | — | CH$_2$ (9) and CH$_2$ (9') |
| 1.38 | Sextet | 4 | — | CH$_2$ (10) and CH$_2$ (10') |
| 0.95 | Triplet | 6 | — | CH$_3$ (11) and CH$_3$ (11') |

EXAMPLE 4
2-Butyl-3-(4-[3-(dibutylamino)propoxy]benzoyl)-5-nitrobenzofuran hydrochloride 4-[3-(Dibutylamino)propoxy]benzoyl chloride hydrochloride obtained in the preceding example 3 is introduced into a round-bottomed flask and then 35.1 g (0.160 mol) of 2-butyl-5-nitrobenzofuran are added. The medium is cooled to between 0 and 3° C. and then 66.9 g (0.4 mol) of ferric chloride are introduced while continuing to cool with an ice/methanol bath. The temperature is maintained at 20 to 22° C. for 1 hour 30 minutes and then the medium is hydrolyzed by addition of 400 ml of demineralized water while maintaining the temperature of the medium between 20 and 25° C. The mixture is separated by settling for 30 minutes and the upper aqueous phase is removed. The organic phase is subsequently washed 5 times using 300 ml of deionized water.

In this way, the desired compound is obtained in the form of an oil.

Yield: approximately 98%.

EXAMPLE 5
2-Butyl-3-(4-[3-(dibutylamino)propoxy]benzoyl]-5-nitrobenzofuran 126.6 g (0.368 mol) of 4-[3-dibutylamino)propoxy] benzoic acid hydrochloride, 600 ml of chlorobenzene and 3 drops of N,N-dimethylformamide are introduced into a 1 l round-bottomed flask. 87.6 g (0.736 mol) of thionyl chloride are introduced over approximately 45 minutes while maintaining the mixture under an inert atmosphere. The mixture is maintained at 85±1° C. for 1 hour, to form 4-[3-(dibutylamino)-propoxy]benzoyl chloride hydrochloride, and then 225 g of a mixture of chlorobenzene and of thionyl chloride are distilled off under gradually increasing vacuum. The reaction medium is cooled to ambient temperature (20 to 22° C.) and then 70.2 g (0.320 mol) of 2-butyl-5-nitrobenzofuran are added. The medium is cooled to between 0 and 3° C. and then 133.8 g (0.8 mol) of ferric chloride are introduced while continuing to cool with an ice/methanol bath.

The temperature rises to approximately 20° C. and is maintained at this value (20 to 22° C.) for 1 hour 30 minutes. The reaction medium is hydrolyzed by addition of 800 ml of demineralized water while maintaining the temperature of the medium between 20 and 25° C. The mixture is separated by settling for 30 minutes and the upper aqueous phase is removed.

The organic phase, comprising the 2-butyl-3-(4-[3-(dibutylamino)propoxy]benzoyl)-5-nitrobenzofuran hydrochloride thus formed, is subsequently washed 5 times using 600 ml of deionized water. It is washed a sixth time with 600 ml of deionized water comprising 50 g (0.595 mol) of sodium hydrogencarbonate to release the desired compound. The chlorobenzene is removed on a rotary evaporator (bath temperature: 35° C., pressure: 10 mmHg).

In this way, 192 g of the desired compound are obtained.

Yield: approximately 95%. Purity (HPLC) Desired compound: 98.3% 4-[3-(Dibutylamino)propoxy]benzoic acid: 0.9% Assay: 80 to 82%

EXAMPLE 6

Dronedarone Hydrochloride

A. 5-Amino-2-butyl-3-(4-[3-(dibutylamino)propoxy]benzoyl)benzofuran

A medium formed of 20.4 g (0.04 mol) of 2-butyl-3-(4-[3-(dibutylamino)propoxy]benzoyl)-5-nitrobenzofuran, prepared as described in example 5, 200 ml of ethanol and 0.6 g of platinum oxide is stirred in a hydrogenation device under a pressure of 3.4 atmospheres ($3.44 \times 10^5$ Pa) of hydrogen. When the pressure reaches 2.7 atm ($2.73 \times 10^5$ Pa), the reaction is terminated, which requires approximately 20 minutes.

In this way, 5-amino-2-butyl-3-(4-[3-(dibutylamino)propoxy]benzoylbenzofuran is obtained.

Yield: 98.4%. Purity (HPLC): 95.28%.

B. Dronedarone

A solution of 17.6 g (0.154 mol) of methanesulfonyl chloride in 375 ml of dichloroethane is added dropwise to a solution of 68.3 g (0.15 mol) of the compound obtained in the preceding paragraph A. and of 23.6 g (0.23 mol) of triethylamine in 750 ml of dichloroethane. The mixture is stirred for 20 hours and is poured into 500 ml of water. The mixture is separated by settling and the organic phase is washed with water and evaporated to dryness. The crude product thus obtained (79.5 g; crude yield: 100%) is purified by elution chromatography on a silica column (eluent: ethyl acetate).

In this way, 48 g of purified dronedarone are collected.

Yield: 61.6%.

Treatment with hexane of the product thus obtained gave a fraction of 44 g in the crystalline state (purity by HPLC: 96.1%) and a fraction of 4 g in the crystalline state (purity by HPLC: 99%).

Yield: 65.3%.

C. Dronedarone Hydrochloride 2 g of dronedarone are dissolved in 40 ml of anhydrous ethyl acetate. A solution of hydrochloric acid in ether is added with stirring until a pH of 3 is reached. After a few minutes, the hydrochloride begins to precipitate. It is filtered off after 0.75 hour, which gives 2.03 g of a white product.

In this way, drondedarone hydrochloride is collected.

M.p.: 143° C. (acetone).

What is claimed is:

1. 2-Butyl-3-(4-[3-(dibutylamino)propoxy]benzoyl)-5-nitrobenzofuran hydrochloride of formula (1)

(1)

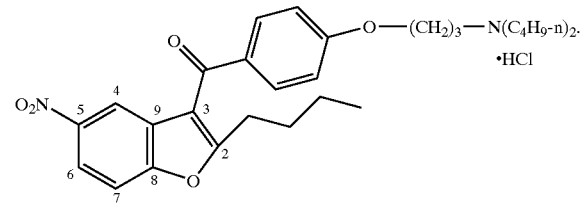

2. A compound of formula (2)

(2)

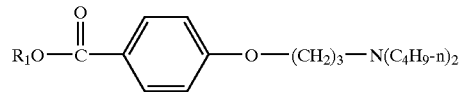

wherein $R_1$ is hydrogen or a $C_1$–$C_4$ alkyl group, or a hydrochloride salt thereof.

3. 4-[3-(Dibutylamino)propoxy]benzoic acid hydrochloride according to claim 2.

4. Methyl 4-[3-(dibutylamino)propoxy]-benzoate according to claim 2.

5. A process for the preparation of 2-butyl-3-(4-[3-(dibutylamino)propoxy]benzoyl)-5-nitrobenzofuran hydrochloride, which comprises the reaction, in an organic phase composed of one or more solvents chosen from halogenated or nonhalogenated hydrocarbons, of 2-butyl-5-nitrobenzofuran with 4-[3-(dibutylamino)propoxy]benzoyl chloride hydrochloride in the presence of a maximum of 3 molar equivalents of a Lewis acid, and then hydrolysis to form the desired compound, which is recovered in the organic phase.

6. A process according to claim 5 wherein the organic phase is composed of one or more solvents chosen from aliphatic, alicyclic or aromatic halogenated hydrocarbons.

7. A process according to claim 5 wherein the Lewis acid is chosen from the group consisting of aluminum chloride, zinc chloride, boron trifluoride, stannic chloride, titanium tetrachloride, ferric chloride and mixtures of these.

8. A process according to claim 7 wherein the Lewis acid is ferric chloride.

9. A process according to claim 8 wherein the Lewis acid is used in a proportion of 2 to 3 molar equivalents.

10. A process according to claim 5 wherein 4-[3-(dibutylamino)propoxy]benzoyl chloride hydrochloride is used in an amount of 1 to 1.3 molar equivalents.

11. A process according to claim 5 wherein the basic agent is sodium hydrogen-carbonate or sodium hydroxide.

12. A process for the preparation of 2-butyl-3-(4-[3-(dibutylamino)propoxy]benzoyl)-5-nitrobenzofuran, which comprises the treatment of 2-butyl-3-(4-[3-(dibutylamino)propoxy]benzoyl)-5-nitrobenzofuran hydrochloride with a basic agent.

13. A process for the preparation of 2-butyl-3-(4-[3-(dibutylamino)propoxy]benzoyl)-5-nitrobenzofuran, which comprises the reaction, in an organic phase composed of one or more solvents chosen from halogenated or nonhalogenated hydrocarbons, of 2-butyl-5-nitrobenzofuran with 4-[3-(dibutylamino)-propoxy]benzoyl chloride hydrochloride in the presence of a maximum of 3 molar equivalents of a Lewis acid as catalyst, and then hydrolysis to produce 2-butyl-3-(4-[3-(dibutylamino)propoxy]benzoyl-5-nitrobenzofuran hydrochloride which is recovered in the organic phase and without isolation is treated with a basic agent to give the desired compound.

14. A process according to claim 13 wherein the organic phase is composed of one or more solvents chosen from aliphatic, alicyclic or aromatic halogenated hydrocarbons.

15. A process according to claim 13 wherein the Lewis acid is chosen from the group consisting of aluminum chloride, zinc chloride, boron trifluoride, stannic chloride, titanium tetrachloride, ferric chloride and mixtures of these.

16. A process according to claim 15 wherein the Lewis acid is ferric chloride.

17. A process according to claim 26 wherein the Lewis acid is used in a proportion of 2 to 3 molar equivalents.

18. A process according to claim 13 wherein 4-[3-(dibutylamino)propoxy]benzoyl chloride hydrochloride is used in an amount of 1 to 1.3 molar equivalents.

19. A process according to claim 13 wherein the basic agent is sodium hydrogen-carbonate or sodium hydroxide.

20. A process for the preparation of dronedarone or a pharmaceutically acceptable salt thereof, which comprises:
   a) the reaction, in an organic phase composed of one or more solvents chosen from halogenated or nonhalogenated hydrocarbons, of 2-butyl-5-nitrobenzofuran with 4-[3-(dibutylamino)propoxy]benzoyl chloride hydrochloride in the presence of a maximum of 3 molar equivalents of a Lewis acid, and then hydrolysis to produce 2-butyl-3-(4-[3-dibutylamino)propoxy]benzoyl-5-nitrobenzofuran hydrochloride which is recovered in the organic phase and treated without isolation with a basic agent to form 2-butyl-3-(4-[3-(dibutylamino)propoxy]benzoyl)-5-nitrobenzofuran,
   b) the hydrogenation of the compound thus obtained in the presence of an appropriate catalyst to give 5-amino-2-butyl-3-(4-[3-(dibutylamino)propoxy]benzoyl-benzofuran, and
   c) the reaction of the 5-aminobenzofuran derivative thus obtained with methanesulfonyl chloride or methanesulfonic anhydride in the presence of an acid acceptor, to give dronedarone, which can be reacted, if desired, with an organic or inorganic acid to form a pharmaceutically acceptable salt of this compound.

21. A process according to claim 20 wherein the organic phase is composed of one or more solvents chosen from aliphatic, alicyclic or aromatic halogenated hydrocarbons.

22. A process according to claim 20 wherein the Lewis acid is chosen from the group consisting of aluminum chloride, zinc chloride, boron trifluoride, stannic chloride, titanium tetrachloride, ferric chloride and mixtures of these.

23. A process according to claim 22 wherein the Lewis acid is ferric chloride.

24. A process according to claim 23 wherein the Lewis acid is used in a proportion of 2 to 3 molar equivalents.

25. A process according to claim 20 wherein 4-[3-(dibutylamino)propoxy]benzoyl chloride hydrochloride is used in an amount of 1 to 1.3 molar equivalents.

26. A process according to claim 20 wherein the basic agent is sodium hydrogen-carbonate or sodium hydroxide.

27. A process for the preparation of 4-[3-(dibutylamino)propoxy]benzoyl chloride hydrochloride, which comprises:
   a) the reaction of 1-dibutylamino-3-chloropropane with a $C_1$–$C_4$ alkyl p-hydroxybenzoate in the presence of a basic agent, to produce a $C_1$–$C_4$ alkyl 4-[3-(dibutylamino)propoxy]benzoate,
   b) the saponification of the ester thus obtained in the presence of an alkali metal hydroxide and then the treatment of the salt thus formed with hydrochloric acid to form 4-[3-(dibutylamino)propoxy]benzoic acid hydrochloride, and
   c) the treatment of the hydrochloride thus obtained with a chlorinating agent, to produce the desired compound.

28. A process according to claim 27 wherein the $C_1$–$C_4$ alkyl p-hydroxybenzoate is methyl p-hydroxybenzoate.

* * * * *